United States Patent [19]
Pierotti

[11] Patent Number: 4,738,827
[45] Date of Patent: Apr. 19, 1988

[54] CAPILLARY TUBE HOLDER FOR TEST INSTRUMENTS ESPECIALLY BLOOD TESTS AND PARTICULARLY FOR PLATELET COUNTERS, WITH TWO COAXIAL CHAMBERS

[75] Inventor: Romano Pierotti, Aiezzo, Italy

[73] Assignee: S.E.A.C.s.r.l., Italy

[21] Appl. No.: 860,055

[22] Filed: May 6, 1986

[30] Foreign Application Priority Data

May 7, 1985 [IT] Italy .............................. 11647/85[U]

[51] Int. Cl.$^4$ ........................... B01L 9/00; G01N 1/12
[52] U.S. Cl. .................................. 422/104; 73/864.02; 73/864.72; 73/864.91; 128/760; 422/100; 422/102
[58] Field of Search ........... 73/864.72, 864.91, 864.02, 73/864.34; 128/760, 763, 765; 422/99, 100, 102, 104

[56] References Cited

U.S. PATENT DOCUMENTS

| | | | |
|---|---|---|---|
| 2,587,221 | 2/1952 | Richardson et al. | 422/102 |
| 3,640,267 | 2/1972 | Hurtig et al. | 73/864.11 |
| 3,837,376 | 9/1974 | Brown et al. | 422/100 |
| 4,162,896 | 7/1979 | Hösli | 73/864.72 |

Primary Examiner—Michael S. Marcus
Attorney, Agent, or Firm—McGlew and Tuttle

[57] ABSTRACT

The phial or vial holding for a capillary tube is internally subdivided into an external chamber having annular cross-section and an internal chamber having circular cross-section. The outer wall of the chamber of annular cross-section carries a capillary hole and the inner tubular wall separating the two chambers has a hole in alignment with that of the outer wall and of larger diameter. In the hollow space of annular cross-section, a slight entrained flow through the hole of the inner wall and consequently a fast removal of the sample liquid which has passed through the capillary hole takes place. This is without backward flow in the direction of the capillary hole.

3 Claims, 1 Drawing Sheet

U.S. Patent   Apr. 19, 1988   4,738,827
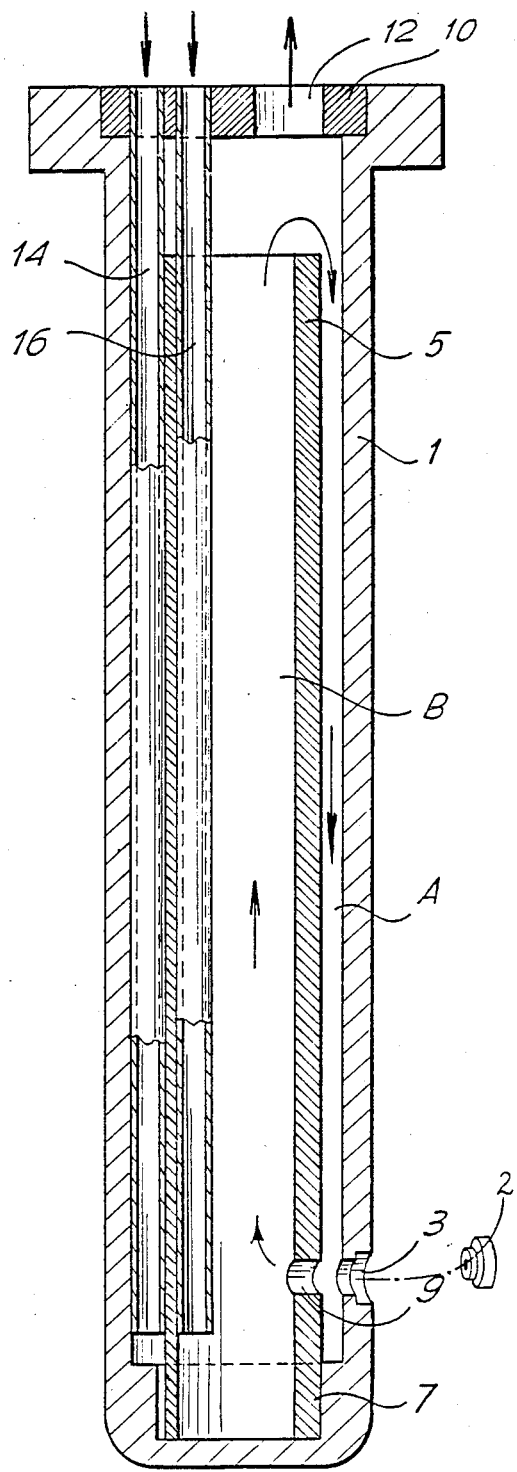

CAPILLARY TUBE HOLDER FOR TEST INSTRUMENTS ESPECIALLY BLOOD TESTS AND PARTICULARLY FOR PLATELET COUNTERS, WITH TWO COAXIAL CHAMBERS

BACKGROUND OF THE INVENTION

Field of the Invention

This invention relates, in general, to holders and, in particular, to a new and useful holder for capillary tubes and phial holders.

The invention refers particularly to a phial or vial for holding capillary tubes that are intended for use with biomedical test instruments and in particular for certain blood tests requiring the counting of cells present in suitably diluted blood. This is particularly but not exclusively, for the counting of thrombocytes or platelets. The basic concept of the present capillary tube holder involves the evaluation of the difference of electrical characteristics which occur within the capillary port or hole upon the passage of a body contained in the sample that is to be counted. The main problem is that of avoiding or at least limiting the error which may occur upon a possible passage of an already counted body—and which has therefore already passed through the capillary tube—in the vicinity of the same capillary tube, which event may cause an electrical signal corresponding to that taking place upon a passage of a body and, hence, may lead to a mistaken count of a further particle.

According to the invention, the phial for holding capillary tubes, or capillary tube holder, is internally subdivided into an external chamber having an annular cross-section and an internal chamber having a circular cross-section most coaxial therewith. The outer wall of the chamber, which has an annular cross-section, carries the capillary port or hole and the inner tubular wall separating the two chambers has a hole disposed in alignment with that of the external capillary hole. The inner hole has a larger diameter than the outer capillary hole. Through suction, the sample liquid is made to enter inside the test tube of the platelet counter through the capillary hole. Soon after its transit into the capillary hole, the sample liquid goes through the annular hollow space and passes through the hole of large diameter, into the tubular inner wall to reach the internal chamber. Inside the hollow space having the annular cross-section, a slight call flow is thus generated through the hole of the tubular inner wall, said flow causing a fast removal of the sample liquid that has gone through the capillary hole with no backward flows in the direction of the outer capillary hole but with relatively very fast transit within the internal chamber defined by the tubular wall and having circular cross-section.

Advantageously, the inner tubular wall is coaxial with the wall of the test tube or phial holding the capillary hole, and the two chambers are widely in communication to each other in their upper parts where the suction takes place.

For the periodic washing, two pipes for the intake at a washing liquid are advantageously provided, one of which reaches the lower part of the hollow space having annular cross-section, while the other reaches the lower part of the internal chamber formed by the tubular wall.

The various features of novelty which characterize the invention are pointed with particularity in the claims anexed to and forming a part of this disclosure. For a better understanding of the invention, its operating advantages and specific objects obtained by its uses, reference is made to the accompanying drawings and descriptive matter in which a preferred embodiment of the invention is illustrated.

BRIEF DESCRIPTION OF THE DRAWINGS

The only FIGURE of the drawings is an axial, sectional view of a phial constructed in accordance with this invention.

GENERAL DESCRIPTION OF THE PREFERRED EMBODIMENT

According to what is illustrated in the drawing, numeral 1 indicates the phial or holder housing with cylindrical wall, which, in its lower part, has a seat forming capillary port means 3 intended to receive and support a capillary hole or port 2. Numeral 5 indicates a tubular wall or wall means inside the cylindrical housing 1 and coaxial therewith, which is engaged—in the lower part at 7—with the bottom of the housing 1 to which it may be glued or otherwise blocked. The tubular wall 5 has an inner hole 9 which is in alignment with the seat 3 and thus with the capillary hole. The hole 9 has a larger diameter than the capillary hole and forms port means for wall 5. The wall 5 delimits an external chamber A of annular cross-section with a relatively very narrow hollow space and an internal chamber B of relatively much larger circular cross-section. On a covering plate 10, a suction or outlet opening 12 is located, through which the diluted blood sample that has passed into the platelet counter, that is, through the capillary hole and the hole 9, is discharged.

The phial housing 1 is dipped into a sample-holding basin (not shown), and, upon suction from passage 12, the diluted sample is caused to transit through the capillary hole or port located in the seat 3 with a relatively violent jet which gives rise to a sample flow going almost directly through the hole 9 of chamber B along with an entrained flow of pure liquid contained in the chamber A at the beginning of the operation. By this mechanism, the sample liquid which has passed through the capillary hole into the seat 3, goes rapidly into the chamber B. From this chamber B, the pure liquid initially held therein, passes form the top into the chamber A to be recalled through the hole 9 by the violent jet of the sample liquid going through the hole 3. The count operation, relative to the sample passing through the capillary hole is performed prior to the filling up of chamber B with the sample liquid, so that pure liquid always enters the chamber A thus avoiding, in practice, any error due to a mistaken count because the passage of particles that have already passed through the capillary hole 9 in the vicinity thereof which would thus alter the signal.

After performing the measurement, that is, the count of the platelets or other particles, washing and refilling of the two chambers A and B with pure liquid is carried out again before performing a further operation. The washing may be performed by introducing washing liquid—which may be pure liquid taking part then in the above-described function—through two pipes 14 and 16 connected to the plate 10. Pipe 14 leads into the lower parts of the hollow space A and the other pipe 16 leads into the lower part of chamber B. The liquid, which is introduced into these two pipes for washing, ensures the complete washing of the two chambers A and B with outflow through the hole 12. A slight pressure takes place inside the two chambers A and B upon the washing phase thereby the capillary hole is also washed with a flow of washing liquid running in a direction opposite to that of the sample liquid when the count operation is performed. Moreover, the very small size of the capillary hole and the limited washing pressure avoid an alteration of the value of the sample dilution even if washing is performed when the container assembly 1 is already dipped into a fresh sample to be tested by the operation, subsequent to the washing step.

While a specific embodiment of the invention has been shown and described in detail to illustrate the application of the principals of the invention, it will be understood that the invention may be embodied otherwise without departing from such principals.

I claim:

1. A capillary tube holder for test instruments comprising, a cylindrically shaped housing having an open upper end, a closed bottom end and capillary port means in an outer wall of the housing adjacent to said closed bottom end; tubular wall means disposed in said housing and dividing an internal volume of said housing into a first centrally disposed chamber and a second concentrically disposed annular chamber, said tubular wall means having one end thereof in contact with said bottom end and having port means adjacent said one end thereof and lying upon a common plane that extends through said capillary port means, said tubular wall port means having a larger cross-sectional flow area then said capillary port means; and closure means adapted to be received in said open end of said housing, said closure means have two inlet means adapted for receiving conduit means and guiding a respective conduit into each of said first and second chambers and an outlet means for connection of said housing to suction means.

2. A capillary tube holder for test instruments comprising, a cylindrically shaped housing having an open upper end, a closed bottom end and capillary port means in an outer wall of the housing adjacent to said closed bottom end; tubular wall means disposed in said housing and dividing an internal volume of said housing into a first centrally disposed chamber and a second concentrically disposed annular chamber, said two chambers being in communication one to the other at the upper end of said housing, said tubular wall means having one end thereof in contact with said bottom end and having port means which are coaxial to said capillary port means, said tubular wall port means having a larger cross-sectional flow area then said capillary port means; and closure means adapted to be received in said open end of said housing, said closure means have a plurality of inlet and outlet means, two of said inlet means adapted for receiving conduit means and guiding a respective conduit into each of said first and second chambers and an outlet means for connection of said housing to suction means.

3. A capillary tube holder for test instruments comprising, a cylindrically shaped housing having a closed upper end, a closed bottom end and capillary port means in an outer wall of the housing; tubular wall means disposed in said housing and dividing an internal volume of said housing into a first centrally disposed chamber and a second annular chamber, said two chambers being in communication one to the other at the upper end of said housing, said tubular wall means having one end thereof in contact with said bottom end and having port means which are coaxial to said capillary port means, said tubular wall port means having a larger cross-sectional flow area than said capillary port means; and said closed upper end of said housing having a plurality of inlet and outlet means, two of said inlet means adapted for receiving conduit means and guiding a respective conduit into each of said first and second chambers and an outlet means for connection of said housing to suction means.

* * * * *